United States Patent [19]
Johnson, Jr.

[11] Patent Number: 4,628,918
[45] Date of Patent: Dec. 16, 1986

[54] PNEUMATIC ARM BAND FOR LOCALIZED ARM PRESSURE

[76] Inventor: Glenn W. Johnson, Jr., 10 Friar Tuck Cir., Summit, N.J. 07901

[21] Appl. No.: 712,745

[22] Filed: Mar. 18, 1985

Related U.S. Application Data

[63] Continuation of Ser. No. 343,094, Jan. 27, 1982, abandoned.

[51] Int. Cl.⁴ .......................... A61F 5/04; A63B 61/00
[52] U.S. Cl. .................... 128/90; 128/89 R; 128/DIG. 20; 128/169; 273/29 R
[58] Field of Search ............ 273/29 R; 128/156, 157, 128/169, 325, 327, 329, DIG. 15; 168/89 R, 90, DIG. 20

[56] References Cited

U.S. PATENT DOCUMENTS

| | | | |
|---|---|---|---|
| 3,120,846 | 2/1964 | Fletcher | 128/327 |
| 3,171,410 | 3/1965 | Towle, Jr. et al. | 128/325 |
| 3,745,998 | 7/1973 | Rose | 128/89 R |
| 3,970,081 | 7/1976 | Applegate, Jr. | 273/29 R |
| 4,027,666 | 6/1977 | Marx | 128/DIG. 15 |
| 4,243,028 | 1/1981 | Puyana | 128/327 |
| 4,273,130 | 6/1981 | Simpson | 128/327 |
| 4,340,042 | 7/1982 | Smith | 128/DIG. 20 |
| 4,345,591 | 8/1982 | Hedgren | 128/169 |

Primary Examiner—C. Fred Rosenbaum
Assistant Examiner—J. L. Kruter
Attorney, Agent, or Firm—S. Michael Bender

[57] ABSTRACT

A band or strap adapted to be circumferentially fitted about the arm to alleviate the symptoms of tennis elbow. The band incorporates inwardly protruding means of limited circumferential extent for applying a radially directed pressure against that portion of the extensor muscle coextensive therewith when the arm band is circumferentially tensioned and fastened in place about the arm. In its preferred form, the means of limited circumferential extent consists of a semi-compressible, inflated air bag carried in a pocket in the arm band. The protruding air bag applies a radially directed pressure or compressive counterforce against the extensor muscle which is of greater magnitude that the pressure exerted against the other circumferential portions of the arm engaged directly by the arm band.

11 Claims, 5 Drawing Figures

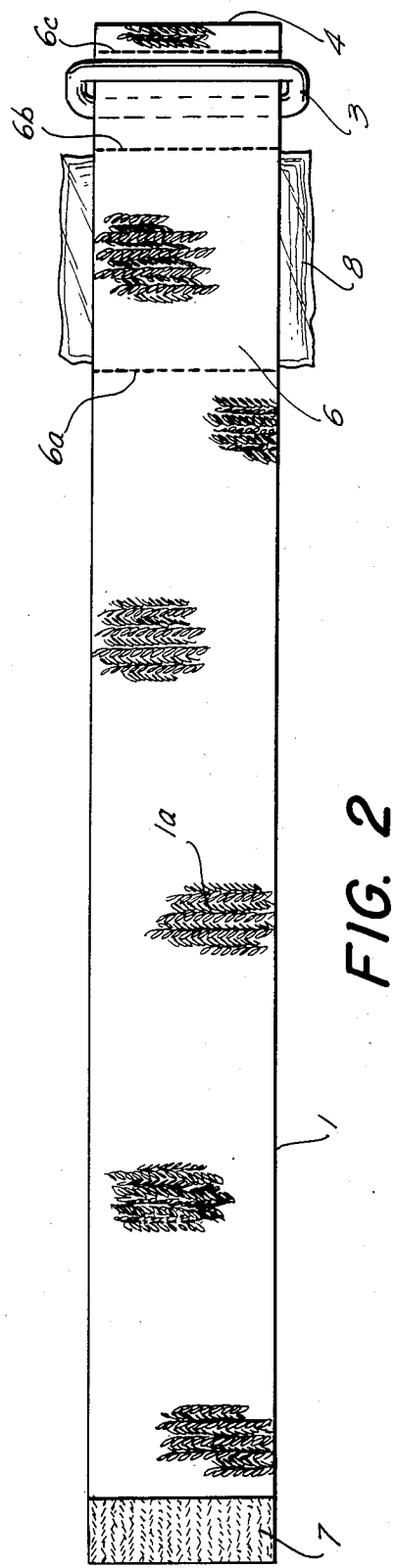
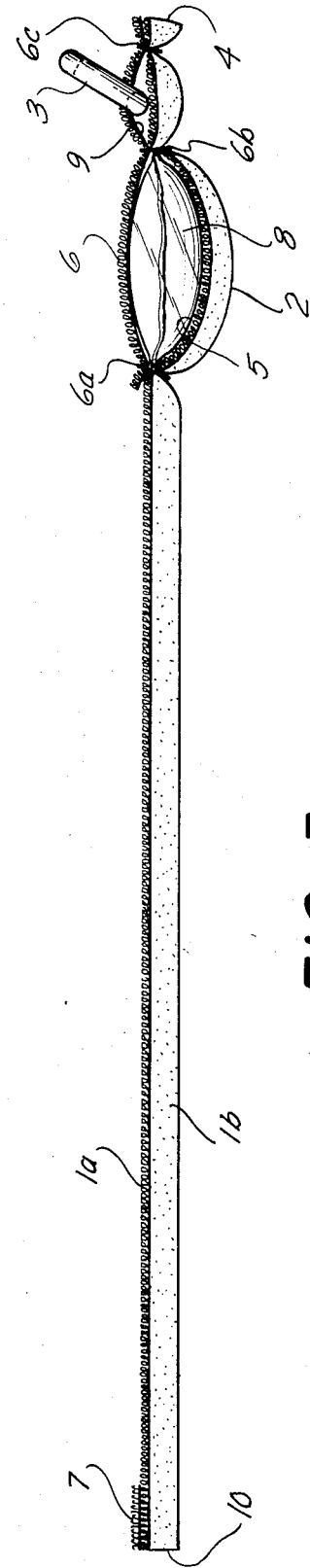

PNEUMATIC ARM BAND FOR LOCALIZED ARM PRESSURE

This is a continuation of application Ser. No. 343,094, filed Jan. 27, 1982, now abandoned.

The present invention relates generally to arm bands, and more specifically to a unique arm band construction adapted to be worn by persons suffering from the symptoms of tennis elbow.

A widely practiced prior method of alleviating discomfort due to a so-called "tennis elbow" condition consists of tightening an in elastic, circumferentially extending band or strap about the affected forearm in the vicinity of the elbow sufficiently to apply a radially directed pressure or compressive counterforce against the extensor muscle when the latter contracts. Since the prior art band, however, applies the same magnitude of radial pressure against the extensor muscle portion of the arm as it applies against the other circumferential portions of the arm coextensive with its extent and displaced from the extensor muscle, considerable discomfort and possibly, interference with blood circulation may result, especially in those cases where a relatively high compressive counterforce is required against the extensor muscle in order to achieve the desired efficacy.

Against the foregoing background, it is the primary object of the present invention to provide an improved arm band which may be used to alleviate the symptoms of tennis elbow. It is another object of the present invention to provide an improved arm band construction which when worn circumferentially about the arm incorporates means for applying a relatively high radially directed pressure or compressive counterforce against the extensor muscle portion of the arm while simultaneously applying a relatively lower radially directed pressure against the other circumferential portions of the arm displaced from the extensor muscle and coextensive with the arm band.

Toward the attainment of these and additional objects and advantages, the present invention, briefly summarized, comprises an arm band adapted to be circumferentially tightened and fastened in place about the extensor muscle on the forearm in the vicinity of the elbow. The arm band incorporates inwardly protruding means of limited circumferential extent relative to the arm band for applying a radially directed pressure or compressive counterforce against that portion of the extensor muscle coextensive with the band when the latter is circumferentially tensioned and fastened in place on the arm. In its preferred form, the inwardly protruding means consists of a compressible, inflated air bag carried in a pocket in the arm band. The inwardly protruding air bag by virtue of its semi-compressible nature, its limited circumferential extent, and the circumferential tension applied to the arm band, causes the air bag to apply a radially directed pressure or compressive counterforce against the extensor muscle of greater magnitude than that directed against other circumferential portions of the arm coextensive with the arm band and displaced from the extensor muscle.

The foregoing and still other features and advantages as well as a more complete understanding of the present invention will be made more apparent from a study of the following detailed description of the preferred form of the invention in connection with the accompanying drawings wherein:

FIG. 2 is a plan view of the preferred embodiment of the arm band of the present invention;

FIG. 3 is a front view of the arm band of FIG. 2;

Figure 1:
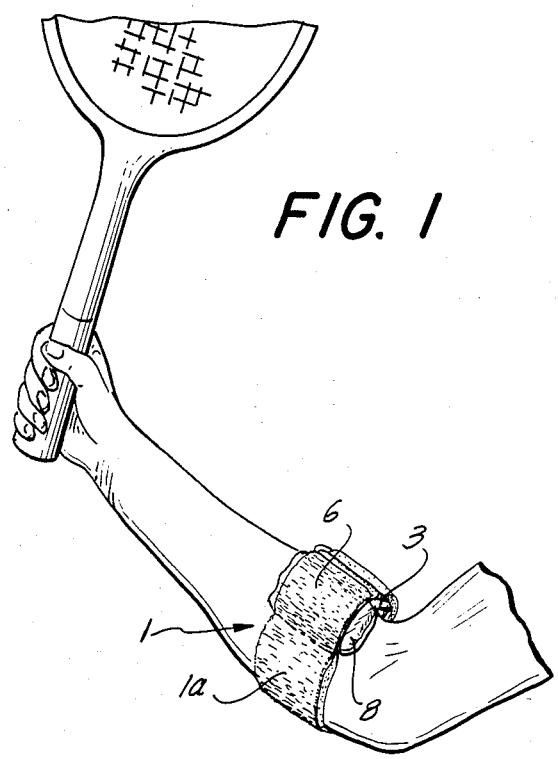
FIG. 1 is a diagramatic representation of the arm band of the present invention fitted about the forearm of a tennis player.

Referring initially to FIG. 1, the arm band of the present invention generally indicated by reference numeral 1, is adapted to be circumferentially fitted on the forearm of a tennis player so as to partially overlie the extensor muscle near the elbow as diagrammatically shown.

Turning to FIGS. 2 and 3, the preferred embodiment of arm band 1 comprises an elongated band or strap having a pair of laminated plies or layers 1a and 1b. Band 1 is preferably fabricated from material commercially available under the trademark VELFOAM and has an upper ply 1a (FIG. 3) of VELCRO fastening hook or loop material bonded to a lower ply 1b of polyurethane foam. This form of belt construction is extremely light in weight, yet of sufficient strength for its intended purpose, and the foam layer or ply 1b which contacts the surface of the player's arm facilitates a high degree of comfort.

Adjacent the right-most end 4 of band 1, a relatively short length of material 6, preferably also of VELCRO hook or loop fastening material, is fastened to band 1 coextensive with upper ply 1a as by sewing along transverse seams 6a, 6b, and 6c (FIG. 2) to form a pair of loops 5 and 9. Loop 5 which extends between transverse seams 6a and 6b is adapted to form a radially protruding pocket for receiving a semi-compressible pressure applying element 8 to be more fully described below, whereas loop 9 which extends between transverse seams 6b and 6c forms a loop for capturing conventional fastening ring 3 substantially as shown in FIGS. 2 and 3. Fastening ring 3 preferably is formed of molded plastic material, but may be formed of other suitable materials such as metal, for example.

Figures 4, 5:
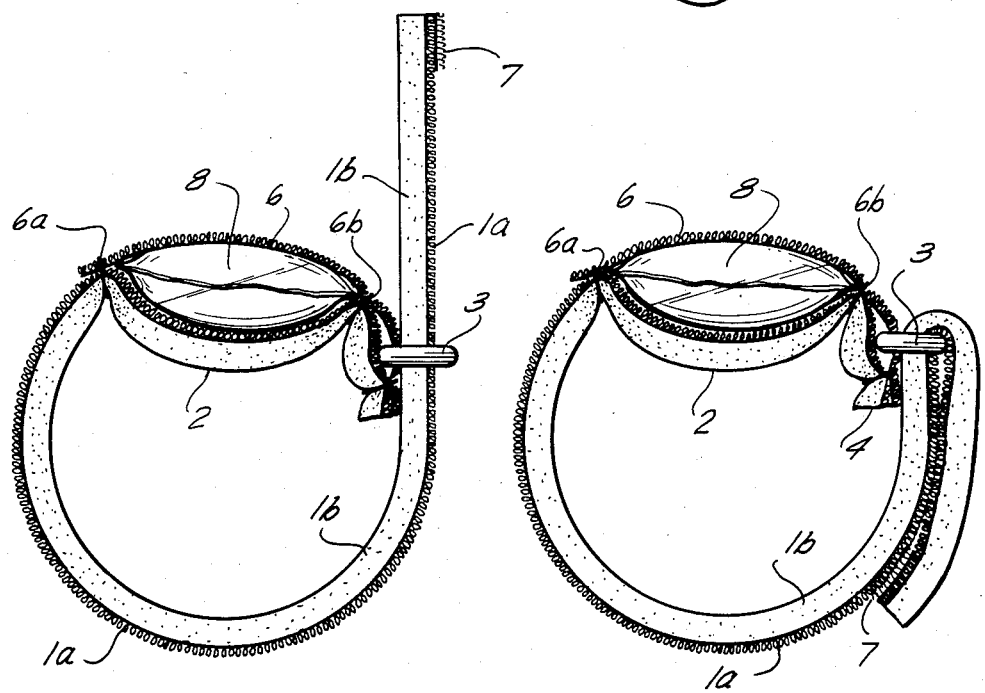
FIG. 4 is a front view of the arm band of FIG. 2 showing the arm band circumferentially positioned about an imaginary arm.
FIG. 5 is a front view of the arm band of FIG. 2 showing the arm band in a circumferentially fastened position about an imaginary arm.

It is important to note that before sewing the short length of material 6 into place to form loops 5 and 9, band 1 is gathered slightly between seams 6a and 6b so that the corresponding portion of material 6 extending between seams 6a and 6b will be slightly shorter in length than the gathered portion 2 of band 1. By this arrangement, the pocket formed by loop 5 will be asymmetrical and will cause element 8 (and gathered portion 2) to protrude radially inwardly toward the central axis of the wearer's arm when the arm band is circumferentially tightened and fastened as best seen in FIGS. 4 and 5.

A fastening element 7 of VELCRO hook or loop material is sewn to upper ply 1a adjacent the left-most end 10 of band 1 as clearly shown in FIGS. 2 and 3.

In accordance with the invention, the pressure applying element 8 preferably consists of a rectangularly shaped inflatable air bag which when inflated is suitably sized to be snugly received into the radially protruding pocket formed by loop 5. As clearly shown in FIG. 2, the transverse extent or major dimension of rectangularly shaped element 8 is greater than the transverse extent of band 1 and thus, the opposed lateral portions of element 8 extend beyond the corresponding side edges of band 1, respectively, when element 8 is so received in the pocket formed by loop 5. Air bag 8 may be fabricated of a pair of thin sheets of flexible plastic material such as polyvinyl chloride heat sealed along their edges and fitted with a self-sealing valve so as to facilitate inflation to varying thicknesses. Such an inflatable air bag is fully described in my prior U.S. Pat. No. 4,287,920 granted Sept. 8, 1981, the disclosure of which is hereby incorporated herein by this reference.

Suffice it to say, for purposes of understanding the present invention, air bag 8 forms a semi-compressible pad adapted to overlie the extensor muscle when the arm band 1 is circumferentially positioned on the forearm of a tennis player as diagrammatically depicted in FIG. 1. The inflated air bag is said to be semi-compressible because although it will conform to the curvature of both the arm band 1 and the wearer's arm when the band is fitted in place under circumferential tension, the air bag 8 will apply a positive radially directed pressure or compressive counterforce uniformly against the portion of the wearer's arm coextensive therewith i.e., the air bag is flexible, but essentially incompressible.

Moreover, and quite surprisingly, I have discovered that the radially directed pressure or compressive counterforce exerted by the air bag 8 against the extensor muscle for a given arm band circumferential tension is substantially greater in magnitude than the radial pressure or compressive force exerted by the band against the other portions of the wearer's arm coextensive with arm band 1 and displaced circumferentially from the protruding air bag. In effect, I have discovered that the protruding air bag pressure element focuses pressure in the region where it is desired or needed, i.e., in the region of the extensor muscle, at the expense of applying pressure to the circumferentially displaced portions of the arm, i.e., the sides and bottom. Also, I have found that the magnitude of radially directed pressure produced by air bag 8 for a given circumferential tension of arm band 1 may be increased by increasing the inflated thickness of the air bag (static). Thus it is possible to select an air bag thickness (e.g., by appropriate inflation pressure) that will focus the desired compressive counterforce in the region of the extensor muscle sufficient to alleviate the symptoms of tennis elbow in a particular person and at the same time require a corresponding circumferential tension in band 1 that is comfortable and without hindrance to blood circulation.

In this regard, and without limiting the present invention, I have found that an arm band having the following nominal dimensions: length 17 inches; transverse width 2 inches; and an air bag fabricated of 12 mil pvc plastic having nominal dimensions of 2.5 inches by 3.0 inches, and an inflated static thickness in the range of about 0.425 inches to about 0.625 inches; will fit most adults, and when circumferentially tightened about an average-sized arm to a firm, yet comfortable level, the radially directed pressure produced by the inflated air bag against the extensor muscle will measure about 40% to 60% greater than the average compression or pressure exerted by the arm band against the other or circumferentially displaced portions of the wearer's arm.

In utilizing the arm band of my invention, the end 10 is loosely slid through fastening ring 3 to permit the arm band to be placed over the wearer's arm in the fashion of a bracelet. The arm band is then positioned so that the inwardly protruding pocket 5 and inflated air bag 8 overlies the extensor muscle on the forearm just below the elbow as diagrammatically indicated in FIG. 1. The arm band is then circumferentially tensioned to a comfortable fit by folding back end 10 of the arm band, pulling against ring 3, and causing VELCRO hooks of element 7 to engage the mating VELCRO loops on the outer surface (ply 1a) of arm band 1. Should a greater amount of pressure be required for a given circumferential tension in arm band 1, air bag 8 may be removed from its pocket by sliding it transversely out of pocket 5, inflated to a greater thickness utilizing the air bag's self-sealing valve, and reinserted into pocket 5. If desired, a small VELCRO fastening element of suitable form may be cemented or otherwise affixed to the surface of air bag 8 to engage with either material 6 or ply 1a and thus facilitate retention of the air bag 8 within pocket 5.

Other obvious variations of the present invention may be made without departing from the spirit or scope of the appended claims. For example, it is believed that other forms of pressure element may be employed in lieu of the inflated air bag 8, such as for example, a semi-compressible pad fabricated of elastomeric material or of polyurathane foam.

I claim:

1. An arm band for alleviating the symptoms of tennis elbow, comprising:

an elongate strap member adapted to be circumferentially tensioned about the forearm of a tennis player in at least partial overlying relation to the extensor muscle thereof, and circumferentially limited means on said strap member for applying a uniform radially directed pressure to said extensor muscle, wherein said circumferentially limited means comprises a pocket protruding inwardly toward said arm, said pocket being in engagement with said at least portion of said extensor muscle when said trap member is fitted about said forearm as aforesaid, a semi-compressible pressure element disposed within said protruding pocket, wherein said semi-compressible pressure element is an inflated air bag, and wherein said pocket comprises a first layer and a second layer disposed coextensively with respect to each other longitudinally of said strap member between a pair of transverse seams, said first layer comprising a portion of the inner circumferential surface of said band so as to engage said at least portion of said extensor muscle when said strap is fitted about said forewarm as aforesaid, said first layer forming an asymetrical pockets, said pocket and said inflated air bag asymetrically protruding radially inwardly when the strap member is circumferentially tensioned about the forearm of said tennis player such that the pressure being applied by said inflated bag in said asymetrically protruding pocket is substantially greater in magnitude then the radially directed pressure applied to portions of the arm spaced from said extensor muscle and coextensive with said strap member when said member is circumferentially tensioned about said forearm as aforesaid.

2. The invention of claim 1 wherein said strap member has a fastening ring at one end thereof, and the other end of said strap member has a fastening element thereon so that said other end may be inserted through said ring to circumferentially tension said strap member about said forearm and said fastening element may be attached to the outer surface of said strap member to maintain said strap member in circumferentially tightened position on said forearm with said inwardly protruding pocket in engagement with said at least portion of said exstensor muscle.

3. The armband of claim 1 wherein said pocket on said strap member has a pair of opposed longitudinally extending openings aligned with said strap member's opposed, spaced side edges, respectively, a rectangular shaped, inflated air bag insertable into said pocket through either of said openings, said inflated air bag having its major dimension parallel to the transverse extent of said strap member and having its minor dimension parallel to the longitudinal axis of said strap member, and fastening means affixed to said one free end of said strap member for cooperating with the other free end of said strap member to fasten said strap member about the forearm of a tennis player in a circumferentially tightened manner after said strap member has been positioned such that said pocket and said inflated air bad engage the extensor muscle of said forearm with the major axis of said rectangularly shaped, inflated air bag aligned parallel to the longitudinal axis of said forearm.

4. The arm band of claim 3 in which the rectangularly shaped, inflated air bag has a major dimension greater than the transverse dimension of said strap member and is disposed in said pocket in such a manner that the opposed longitudinally extending edge portions of said air bag extend beyond the corresponding side edges of said strap member, respectively.

5. The arm band of claim 4 wherein the major dimension of said inflated air bag is about 3.0 inches, the transverse dimension of said strap member is about 2.0 inches, and the longitudinal extent of said pocket on said strap member and the minor dimension of said air bag are about 2.5 inches.

6. The arm band of claim 5 wherein said air bag comprises a pair of thin sheets of flexible material bonded together along their peripheral edges, said air bag being inflated to a thickness in the range of about 0.425 inches to about 0.625 inches to form an incompressible, conformable pressure pad.

7. The arm band of claim 3 wherein said fastening means includes a ring fastened to said free end of said strap member and a VELCRO fastener member affixed to the other free end of said strap member on said upper ply whereby said other free end may be passed through said ring and the VELCRO fastener member thereon may matingly engage the VELCRO material of said upper ply.

8. The method of alleviating the symptoms of tennis elbow comprising the steps of:
(a) providing an inflatable aircell,
(b) inflating said aircell,
(c) providing an elongate arm band having a pocket to receive said inflated aircell disposed along the longitudinal extent thereof, said aircell being sized to engage the extensor muscle of the forearm of a tennis player,
(d) inserting said aircell in said pocket either before, after, or during said step (b),
(e) circumferentially positioning said arm band on said forearm with the inflated aircell in engagement with said extensor muscle in the vicinity of the elbow,
(f) circumferentially tightening said arm band sufficient to cause said inflated aircell to apply a radial supporting pressure inwardly against said extensor muscle uniformly along the extent of said inflated aircell coextensive with the portion of said extensor muscle engaged thereby, and
(g) fastening said arm band in said circumferentially tightened condition about said forearm.

9. The method of claim 8 wherein said aircell is rectangularly shaped and has its major dimension normal to the longitudinal extent of said arm band, and its minor dimension parallel to the longitudinal extent of said arm band, further comprising the step of circumferentially positioning said arm band on said forearm such that the aircell in engagement with said portion of said extensor muscle has its major dimension algined with the longitudinal axis of said forearm and its minor dimension aligned with the longitudinal axis of said strap.

10. An arm band for alleviating the symptoms of tennis elbow, comprising:
an elongate strap member adapted to be circumferentially tensioned about the forearm of a tennis player in at least partial overlying relation to the extensor muscle thereof, and circumferentially limited means on said strap member for applying a uniform radially directed pressure to said extensor muscle,
wherein said circumferentially limited means comprises a pocket protruding inwardly toward said arm, said pocket being in engagement with said at least portion of said extensor muscle when said strap emmber is fitted about said forearm as aforesaid,
a semi-compressible pressure element disposed within said protruding pocket,
wherein said semi-compressible pressure element is an inflated air bag, and
wherein said pocket comprises a first layer and a second layer disposed coextensively with respect to each other longitudinally of said strap member between a pair of transverse seams, said first layer comprising a portion of the inner circumferential surface of said band so as to engage said at least portion of said extensor muscle when said strap is fitted about said forearm as aforesaid, said first layer comprising an upper ply of material joined to a bottom ply of material different from that of said upper ply, said different material being selected to engage the arm of said tennis player and wherein said second layer also is of the same material as said upper ply and is affixed to said upper ply at opposite ends thereof along said transverse seams respectively, to form said pocket.

11. The arm band of claim 10 wherein said upper ply is of hook or loop fastener material and said bottom ply is of foamed thermoplastic.

* * * * *